ખ
United States Patent [19]

Lajoie et al.

[11] Patent Number: 5,518,727
[45] Date of Patent: May 21, 1996

[54] ULTRAFINE SODIUM BICARBONATE POWDER

[75] Inventors: M. Stephen Lajoie, Basking Ridge; Anthony E. Winston, East Brunswick, both of N.J.

[73] Assignee: Church & Dwight Co., Inc., Princeton, N.J.

[21] Appl. No.: 248,687

[22] Filed: May 25, 1994

Related U.S. Application Data

[62] Division of Ser. No. 53,800, Apr. 27, 1993, Pat. No. 5,411,750.

[51] Int. Cl.$^6$ .................................................. A61K 9/14
[52] U.S. Cl. ............................. 424/400; 424/65; 424/404; 424/405; 424/717; 23/293 A; 423/422
[58] Field of Search ........................... 424/405, 409, 424/489, 717; 23/293 A; 423/422

[56] References Cited

U.S. PATENT DOCUMENTS 1,689,697  10/1928  Thornton ........................... 23/293 A
5,108,726  4/1992  Baldwin et al. ..................... 423/279

FOREIGN PATENT DOCUMENTS 1595769  8/1981  United Kingdom ............... 23/293 A

OTHER PUBLICATIONS

Powdering Liquids by Spray–Pro published Mar./Apr., 1926.

*Primary Examiner*—Thurman K. Page
*Assistant Examiner*—Neil Levy
*Attorney, Agent, or Firm*—Depaoli & Frenkel

[57] ABSTRACT

This invention provides alkali metal bicarbonate powder consisting of a narrow size distribution range of ultrafine particles. The ultrafine powder has a large surface area, and provides enhanced reactivity in applications such as deodorization or neutralization, and exhibits increased antibacterial/antifungal activity. The ultrafine powder also has an exceptional capability to form a homogenous solid-phase suspension in a liquid medium which has long term stability.

2 Claims, No Drawings

ULTRAFINE SODIUM BICARBONATE POWDER

This application is a division of application Ser. No. 08/053,800, filed Apr. 27, 1993, U.S. Pat. No. 5,411,750.

BACKGROUND OF THE INVENTION

It is known that the physicochemical properties of solids in particulate form are influenced by the size and shape of the particles. As particle size of solids diminishes in scale, there is an enhancement of properties, and often the inception of new properties. Investigators are finding that nanostructural materials can exhibit unique mechanical, electronic and optical properties.

New commercial products are becoming available which provide special advantage because of fine particle size. Zinc oxide is widely utilized as an ingredient in human health products. Superior results are now obtained by the use of submicron transparent zinc oxide powder. The ultrafine zinc oxide provides advantage for UVA/B-protection in cosmetic formulations, and exhibits enhanced antimicrobial capacity and functions as a preservative.

Alkali metal bicarbonate is another commodity reagent which has found application in a broad variety of products such as laundry detergents, deodorizers, creams and lotions, dentifrices, antacids, buffers, fungicides, and the like.

There is evidence that fine particle size alkali metal bicarbonate can exhibit increased reactivity in comparison with coarse grain alkali metal bicarbonate. In soda cracker production, finely divided sodium bicarbonate ingredient is more efficiently distributed and effectively reactive during the cracker dough preparation. The finished baked cracker is an improved product which has a substantially uniform texture, flavor and surface color, and a consistent pH throughout.

There is continuing interest in the development of reagents such as alkali metal bicarbonate which have an ultrafine particle size, and exhibit a novel combination of properties when utilized as an ingredient in personal care, biologically active, household, and specialty type products.

Accordingly, it is an object of this invention to provide particulate alkali metal bicarbonate having an ultrafine particle size, and a surface area of at least about four square meters per gram.

It is another object of this invention to provide alkali metal bicarbonate powder having a submicron particle size, and exhibiting transparency in the visible light range.

Other objects and advantages of the present invention shall become apparent from the accompanying description and examples.

Publications of background interest with respect to the present invention subject matter include U.S. Pat. Nos. 2,378,147; 3,241,977; 4,997,454; and 5,147,631.

DESCRIPTION OF THE INVENTION

One or more objects of the present invention are accomplished by the provision of an alkali metal bicarbonate powder which consists of ultrafine monoclinic crystalline particles having an average particle size less than about two microns, a surface area between about 5–12 square meters per gram, and a loose bulk density between about 0.07–0.5 gram per cubic centimeter.

In another embodiment this invention provides an alkali metal bicarbonate powder which consists of submicron monoclinic crystalline particles having an average particle size less than about one micron, a surface area between 6–15 square meters per gram, and a loose bulk density between about 0.05–0.2 gram per cubic centimeter.

A present invention submicron alkali metal bicarbonate powder typically consists of particles having an average particle size between about 100–800 nanometers, and a transparency in the visible light range between about 400–700 nanometer wavelength.

A present invention ultrafine powder consists of sodium bicarbonate particles or potassium bicarbonate particles, or a mixture thereof in a ratio between about 5–95 weight percent of each salt ingredient.

The terms "average particle size" and "average diameter" as employed herein refers to the average of the largest dimension of particles.

Several procedures can be employed to prepare ultrafine alkali metal bicarbonate powders. The particle shape and particle size distribution of a powder depends directly on the particular method of preparation.

A present invention alkali metal bicarbonate powder can be obtained in the form of cohesive agglomerated crystallites of primary particles. The agglomerated crystallites can have an average diameter between about 1–10 microns.

One method of preparation involves the dissolution of alkali metal bicarbonate in water at 20°–60° C., and the subsequent addition of a water-miscible organic solvent to the aqueous solution to precipitate primary particles of alkali metal bicarbonate, which aggregate to form cohesive agglomerated crystallites. The average size of the primary particles typically is about 0.5–2 microns, and the average agglomerated crystallite size is 4–12 microns.

Submicron alkali metal bicarbonate can be obtained by employing a variation of the precipitation procedure. This method of preparation involves the addition of a dilute aqueous solution of alkali metal bicarbonate to a water-miscible organic solvent such as methanol, ethanol, tetrahydrofuran, acetone, N,N-dimethylformamide, and the like.

An important aspect of the precipitation procedure for preparation of submicron alkali metal bicarbonate is the use of a dilute aqueous solution of alkali metal bicarbonate. Preferably the aqueous solution has a salt concentration of five weight percent or less.

This type of precipitation procedure yields alkali metal bicarbonate particles which have a narrow size distribution range between about 0.1–1 micron. A smaller particle size is obtained if the solute dissolved in the aqueous medium is a mixture of sodium bicarbonate and potassium bicarbonate.

Alkali metal bicarbonate having a nanometer scale particle size distribution can be prepared by spray-drying a dilute aqueous solution of the salt. An aqueous solution of about 0.1–10 weight percent of alkali metal bicarbonate which is spray-dried as a fine mist can provide alkali metal bicarbonate powder with an average particle size in the range between about 100–800 nanometers. The size of the aqueous mist droplets preferably is less than about 50 microns in diameter, and the spray-drying can be conducted at a temperature between about 80°–160° C.

A mixture of sodium bicarbonate and potassium bicarbonate in solution yields smaller spray-dried particles than does a single bicarbonate salt ingredient. Each component in the mixture can vary between about 10–90 weight percent of the mixture.

Another method of preparing ultrafine alkali metal bicarbonate powder involves the cooling of a saturated aqueous solution of alkali metal bicarbonate while sonicating the solution.

Another method of preparing ultrafine alkali metal bicarbonate is to introduce a stream of carbon dioxide in an aqueous solution of alkali metal carbonate which has a content of water-miscible organic solvent.

A present invention alkali metal bicarbonate powder exhibits a novel combination of properties because of its ultrafine particle size when utilized as an ingredient in personal care and specialty type products.

A present invention submicron alkali metal bicarbonate ingredient enhances odor absorption and neutralization in personal care products, such as those adapted for skin care, oral care or feminine hygiene usage.

A present invention submicron alkali metal bicarbonate ingredient provides improved esthetics in creams, lotions, gels, ointments, soapbars, toothpastes, and the like. Irritation is minimized, skin mildness is improved, and antibacterial/antifungal activity is increased.

Another valuable property of a present invention submicron alkali metal bicarbonate powder is an exceptional capability to blend readily into suspension formulations with other ingredients. The ultrafine size and high surface area of the particles facilitate the formation of a homogenous solid-phase suspension in a liquid medium which has long term stability.

A thin film of submicron alkali metal bicarbonate powder absorbs or scatters ultraviolet light in the 250–375 nanometer range, but is transparent in the 400–700 nanometer wavelength range of visible light.

Standard procedures are followed for measurement of the physical properties of the ultrafine particles.

Surface area is determined by the nitrogen absorption method of Brunauer, Emmett and Teller (BET) as described in J.A.C.S, 60, 309 (1938).

Particle size is determined by transmission electron microscopy, or by X-ray diffractometry.

Loose bulk density is determined by weighing a quantity of powder in a measuring cylinder, inverting the cylinder 10 times to remove air pockets, and reading the final settled volume in cubic centimeters.

In another embodiment this invention provides an alkali metal bicarbonate powder product which consists of monoclinic crystalline particles having an average particle size between about 20–150 microns, and having surfaces coated with between about 0.5–20 weight percent of adherent ultrafine alkali metal bicarbonate particles having an average particle size between about 0.5–10 microns.

Both the primary particles and the adherent surface particles can consist of sodium bicarbonate particles or potassium bicarbonate particles or a mixture thereof.

In a further embodiment this invention provides an alkali metal bicarbonate powder product which consists of monoclinic crystalline particles having an average particle size between about 20–150 microns, and having surfaces coated with between about 0.5–20 weight percent of adherent submicron zinc oxide or zinc sulfide particles having an average particle size between about 10–500 nanometers. The particle size distribution of the adherent zinc oxide or zinc sulfide preferably is in the range between about 5–200 nanometers.

A coated alkali metal bicarbonate powder can be obtained by physically blending the larger matrix particles with the submicron particles, whereby an adherent coating of submicron particles is formed on the surfaces of the matrix particles.

A coated alkali metal bicarbonate powder also can be obtained by suspending the larger matrix particles in an aqueous solution of alkali metal bicarbonate, and adding a water-miscible solvent such as methanol to the aqueous solution to precipitate ultrafine particles of alkali metal bicarbonate onto the surfaces of the suspended matrix particles.

The following examples are further illustrative of the present invention. The components and specific ingredients are presented as being typical, and various modifications can be derived in view of the foregoing disclosure within the scope of the invention.

EXAMPLE I

This Example illustrates the preparation of ultrafine alkali metal bicarbonate powder by a precipitation method in accordance with the present invention.

A 5 weight percent aqueous solution of sodium bicarbonate is added dropwise to a stirred volume of ice-cooled methanol solvent. The addition is continued until about 20 percent by volume of aqueous solution has been admixed. The resultant monoclinic needles are collected by filtration, and dried under vacuum at 60° C.

The primary acicular particles have a size distribution substantially in the range of 0.2–2 micron, and a surface area of about 10 square meters per gram (BET; ASTM D3663-78).

EXAMPLE II

This Example illustrates the preparation of submicron alkali metal bicarbonate powder by a spray-dry method in accordance with the present invention.

An aqueous solution is prepared which contains 3 grams of sodium bicarbonate and 3 grams of potassium bicarbonate per 100 grams of water.

The aqueous solution is sprayed as a fine mist through an inlet nozzle located in the central section of a cylindrical tower which contains air heated at 140° C. The contained column of air has a slow upward flow, at a rate which carries water vapor upward and through an outlet near the top of the tower, and permits the countercurrent settling of crystalline alkali metal bicarbonate particles to a cool collection zone in the bottom of the tower.

The sprayed mist has a droplet size of about 10–15 microns in diameter. The alkali metal bicarbonate particles have a size distribution substantially in the range of about 100–800 nanometers, and a surface area of about 12 square meters per gram (BET).

EXAMPLE III

This Example illustrates a pilot-plant procedure for the preparation of an antiperspirant-deodorant cosmetic stick product which utilizes a ultrafine alkali metal bicarbonate ingredient in accordance with the present invention.

A stainless steel tank is provided which is equipped with turbine agitation.

Silicone oil DC 245 (600 lbs, Dow Corning) is charged to the mixing tank. Agitation (55–65 RPM) is initiated, and heating the liquid medium to 176° F. is commenced.

During the heating period, the following order of ingredients are added to the stirred liquid medium:

|  | lbs. |
| --- | --- |
| Diisopropyl adipate | 60 |
| PPG 14 butyl ether (Americol) | 40 |
| Stearyl alcohol | 340 |
| Castor wax (MP-70) | 60 |
| Eicosanol | 10 |
| PEG 600 distearate (Mazer) | 40 |

The mixture is stirred at 154° F. for about 30 minutes until the ingredients are melted and the liquid medium is homogeneous. The stirring speed is reduced to about 35 RPM, then Cab-o-sil M-5 (15 lbs, Cabot) and aluminum zirconium tetrachlorohydrex (480 lbs. Reheis) are added. The temperature is maintained at 154° F. for about 40 minutes until the fluid medium is uniform, and then the temperature is lowered to 124° F.

Ultrafine sodium bicarbonate powder (140 lbs) and a fragrance (6 lbs, 1FF 567-AT) respectively are added with stirring to Silicone oil DC 245 (245 lbs, Dow Corning) in a second mixing tank at a temperature of 124° F. to form a homogeneous suspension medium. The ultrafine sodium bicarbonate powder is prepared by a precipitation method as described in Example I, and has a particle size distribution substantially in the range of 0.2–2 micron.

The contents of the two mixing tanks which contain heated fluid medium are transferred to separated fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

A second deodorant cosmetic stick product is prepared by eliminating the antiperspirant ingredient, and increasing the quantity of ultrafine sodium bicarbonate ingredient from 140 lbs to 180 lbs in the above described manufacturing process.

The ultrafine sodium bicarbonate ingredient remains homogeneously distributed in the organic matrix during the manufacture and storage of the deodorant stick product.

EXAMPLE IV

This Example illustrates the preparation of a soda cracker product with improved qualities in accordance with the present invention.

| Formula % | Flour Basis % | Ingredients |
| --- | --- | --- |
|  |  | Sponge |
| 40.65 | 60.00 | Soft Wheat Flour |
| 19.65 | 29.00 | Water |
| 0.06 | 0.09 | Instant Yeast |
| 0.39 | 0.50 | Water |
|  |  | Dough |
| 27.10 | 40.00 | Soft Wheat Flour |

| Formula % | Flour Basis % | Ingredients |
| --- | --- | --- |
| 2.71 | 4.00 | Cracker Meal |
| 6.78 | 10.00 | Oil |
| 1.02 | 1.50 | Malt Syrup, Diastatic |
| 1.02 | 1.50 | Salt |
| 0.68 | 1.00 | Sodium Bicarbonate |
| 100.00 | 147.59 | TOTAL |

The instant yeast is dissolved in the minor portion of water, and the sponge ingredients are mixed in a dough trough at 27 rpm with a spindle mixer. The sponge is allowed to rest for about 18 hours at 75°–85° F. with 70–80% relative humidity.

The sponge and dough ingredients are mixed in a dough trough for 3–4 minutes at 27 rpm. The dough is allowed to rest for about 6 hours at 75°–85° F. with 78–80% relative humidity.

The dough is passed through a 3 roll dough sheeter and laminated with 608 layers. The laminated dough is passed through two sets of reducing rollers to achieve a dough thickness of about two millimeters. The dough is shaped and cut into units, and the tops of the shaped dough units are lightly salted.

The shaped dough units are baked at temperatures over a range of about 510°–600° F. for 2–4 minutes in a direct fired traveling band oven with a wire mesh band.

Submicron sodium bicarbonate powder is used as an ingredient in comparison with large particle size sodium bicarbonate powders. The submicron powder is prepared by a spray-dry method as described in Example II.

The submicron sodium bicarbonate powder has a particle size distribution substantially in the range of 0.2–0.6 micron. Two comparative sodium bicarbonate powders have an average particle size of 70 micron and 100 microns, respectively.

The baked soda crackers produced with the present invention submicron sodium bicarbonate have a superior combination of color, texture and flavor properties as compared with the soda crackers produced with the 70 micron and 100 micron sodium bicarbonate ingredients.

EXAMPLE V

This Example illustrates the preparation of a surface-coated alkali metal bicarbonate powder product in accordance with the present invention.

Sodium bicarbonate (100 g, 70 micron average particle size, Church & Dwight) is blended with sodium bicarbonate (10 g, 0.8 micron average particle size) at room temperature over a period of 20 minutes in a rotary blender.

A homogeneous powder is obtained in which the ultrafine particles are present as an adherent coating on the surfaces of the larger matrix particles.

The preparation is repeated, except that zinc oxide (10 g, 5–15 nanometer particle size range, Sachtleben Chemie) is employed as the ultrafine coating solids.

What is claimed is:

1. A process which comprises spray-drying a mist of aqueous alkali metal bicarbonate solution to form alkali metal bicarbonate powder having an average particle size between about 100–800 nanometers; wherein the aqueous solution contains between about 0.1–10 weight percent of alkali metal bicarbonate, and the aqueous mist has a droplet size less than about 50 microns in diameter, and the spray-drying is conducted at a temperature between about 80°–160° C.

2. A process in accordance with claim 1 wherein the alkali metal bicarbonate in solution is a mixture of sodium bicarbonate and potassium bicarbonate, and each bicarbonate is between about 10–90 weight percent of the mixture.

* * * * *